US011129652B2

(12) United States Patent
Rezach et al.

(10) Patent No.: US 11,129,652 B2
(45) Date of Patent: Sep. 28, 2021

(54) ADJUSTABLE-HEIGHT BONE PLATE SYSTEM

(71) Applicant: WARSAW ORTHOPEDIC, INC., Warsaw, IN (US)

(72) Inventors: William Alan Rezach, Covington, TN (US); Joshua Simpson, Collierville, TN (US); David H. Browning, Cordova, TN (US); Richard A. Hynes, Melbourne Beach, FL (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 240 days.

(21) Appl. No.: 16/386,328

(22) Filed: Apr. 17, 2019

(65) Prior Publication Data
US 2020/0330139 A1  Oct. 22, 2020

(51) Int. Cl.
*A61B 17/80* (2006.01)
*A61B 17/70* (2006.01)

(52) U.S. Cl.
CPC ...... *A61B 17/8023* (2013.01); *A61B 17/7059* (2013.01); *A61B 17/8014* (2013.01); *A61B 17/8033* (2013.01); *A61B 17/8057* (2013.01)

(58) Field of Classification Search
CPC .................. A61B 17/8023; A61B 17/7055
See application file for complete search history.

(56) References Cited

U.S. PATENT DOCUMENTS

| 8,080,010 | B2* | 12/2011 | Schulz ................ A61B 17/151 |
| | | | 606/70 |
| 9,707,013 | B2 | 7/2017 | Rezach et al. |
| 9,872,711 | B2 | 1/2018 | Hynes et al. |
| 9,883,948 | B2 | 2/2018 | Chavarria et al. |
| 9,949,776 | B2 | 4/2018 | Mobasser et al. |
| 9,962,171 | B2 | 5/2018 | Rezach et al. |
| 9,962,192 | B2* | 5/2018 | Hawkins ............ A61B 17/7035 |
| 9,974,569 | B2 | 5/2018 | Lehmann, Jr. et al. |
| 9,993,270 | B2 | 6/2018 | Butler |
| 10,028,770 | B2 | 7/2018 | Rezach et al. |
| 10,172,650 | B2 | 1/2019 | Hynes et al. |
| 2006/0241596 | A1 | 10/2006 | Rezach |
| 2007/0233138 | A1 | 10/2007 | Figueroa et al. |
| 2012/0065691 | A1 | 3/2012 | Simonson |
| 2017/0245898 | A1 | 8/2017 | May et al. |

FOREIGN PATENT DOCUMENTS

JP  2004-512899  4/2004

OTHER PUBLICATIONS

U.S. Appl. No. 16/287,700, filed Feb. 27, 2019 in the name of Rezach et al.
(Continued)

*Primary Examiner* — Andrew Yang

(57) ABSTRACT

An adjustable-height bone plate system that can be attached to a bony structure (e.g., the sacrum) is provided. The adjustable-height bone plate system affords height adjustment of a screw head portion to facilitate attachment of a receiver portion and a spinal rod at a proper, recommended, or desired height for secure interconnection of the spinal rod with a receiver of a pedicle screw assembly attached to an adjacent bony structure (e.g., L5 of the lumbar spine).

22 Claims, 12 Drawing Sheets

(56) References Cited

OTHER PUBLICATIONS

U.S. Appl. No. 16/380,739, filed Apr. 10, 2019 in the name of Rezach et al.
U.S. Appl. No. 16/395,319, filed Apr. 26, 2019 in the name of Wickham et al.
U.S. Appl. No. 16/395,409, filed Apr. 26, 2019 in the name of Wickham et al.
U.S. Appl. No. 15/843,938, filed Dec. 15, 2017 in the name of May et al.
International Search Report and Written Opinion dated Feb. 11, 2020 from corresponding International Application No. PCT/US2019/057576.

* cited by examiner

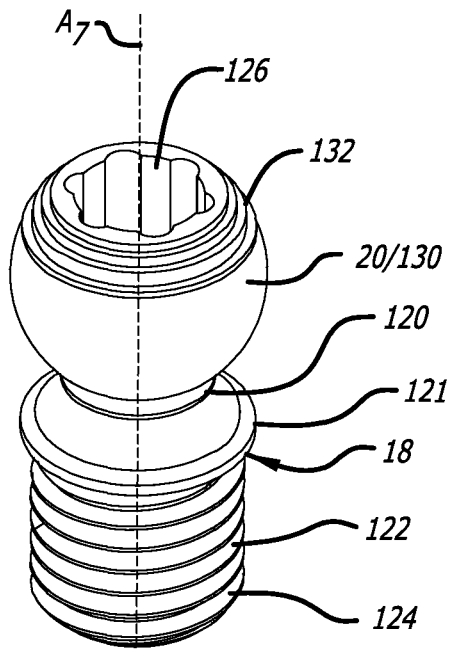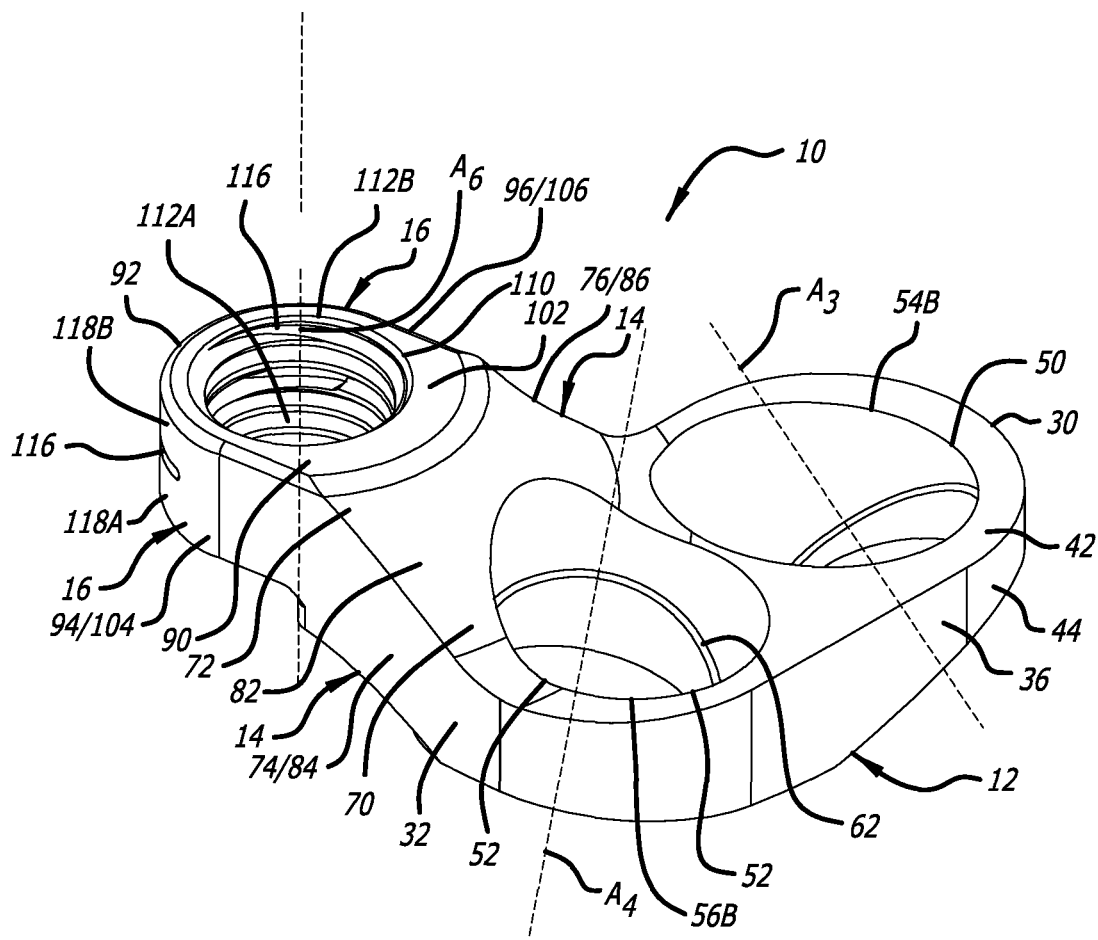
FIG. 3

ADJUSTABLE-HEIGHT BONE PLATE SYSTEM

FIELD

The present technology is generally related to an adjustable-height bone plate system.

BACKGROUND

Surgical rods are commonly used in surgically correcting spinal abnormalities. Typically, pedicle screw assemblies are used to facilitate placement and attachment of the spinal rods relative to the spine. Such pedicle screw assemblies include at least a bone screw section and a receiver portion attached to one another. The bone screw sections are attached to vertebrae, and the receiver portions receive portions of the spinal rods. Furthermore, the receiver portions of typical pedicle screw assemblies are angularly and fixedly positionable with respect to the screw sections to afford attachment of the spinal rods between vertebrae. Oftentimes, however, severe spinal abnormalities do not afford positioning of pedicle screw assemblies so that the spinal rods can be adequately attached between adjacent bony structures. To illustrate, spinal abnormalities can result in the pedicle screw assemblies attached to adjacent bony structures being offset in heights relative to another to a degree that does not facilitate adequate attachment of the spinal rods. For example, the transition between the lumbar spine and the sacrum can provide such an unwanted offset in heights. Therefore, there is a need for an adjustable-height bone plate system that can be attached to a bony structure (e.g., the sacrum) to afford height adjustment of a screw head portion to facilitate attachment of a receiver portion and a spinal rod at a proper, recommended, or desired height for secure interconnection of the spinal rod with a receiver of a pedicle screw assembly attached to an adjacent bony structure (e.g., L5 of the lumbar spine).

SUMMARY

The techniques of this disclosure generally relate to one or more adaptors usable with sacral pedicle screws or other types of anatomy buttressing.

In one aspect, the present disclosure provides a system including a plate body section having a first end, a second end, a first side, a second side, a lower surface, an upper surface, a first thickness between the lower surface and the upper surface, and at least one aperture extending between the lower surface and the upper surface, portions of the first end and the second end being opposite from one another, portions of the first side and the second side being opposite from one another, the lower surface being configured to contact bone, and the at least one aperture being configured to receive a bone screw to facilitate attachment of the plate body section to bone; a plate head section having a first end, a second end, a lower surface, an upper surface, a second thickness between the lower surface and the upper surface of the plate head section, and an aperture extending between the lower surface and the upper surface of the plate head section; and a plate neck section including a first end and a second end opposite from one another, the first end being attached to the plate body section, the second end being attached to the plate head portion, the plate neck portion extending upwardly and outwardly from the plate body section; where the plate neck portion spaces the upper surface of the plate head section from the upper surface of the plate body section at least a first height, and wherein a screw head portion of a screw section is positionable upwardly and downwardly via rotation of the screw section relative to the aperture in the plate head portion between a minimum second height and a maximum third height relative to the upper surface of the plate head section, the third height being greater than the second height, and the second height being greater than the first height.

In another aspect, the disclosure provides a system including a plate body section attachable to bone, the plate body section having a first end, a second end, a first side, a second side, a lower surface, an upper surface, at least a portion of the first end and the second end of the plate body section being opposite from one another, and at least a portion of the first side and the second side being opposite from one another, and the lower surface of the plate body section being configured to contact bone; a plate head section having a first end, a second end, a lower surface, an upper surface, a thickness between the lower surface and the upper surface of the plate head section, and an aperture extending between the lower surface and the upper surface of the plate head section; and a plate neck portion including a first end and a second end opposite from one another, the first end being attached to the plate body section, the second end being attached to the plate head section, the plate neck portion extending upwardly and outwardly from the plate body section to space the plate body section and the plate head section apart from one another; where a screw head portion of a screw section is positionable upwardly and downwardly via rotation of the screw section relative to the aperture in the plate head portion between a minimum first height and a maximum second height relative to the upper surface of the plate head section, the second height being greater than the first height.

In yet another aspect, the disclosure provides a system including a plate body section attachable to bone; a plate head section having a first end, a second end, a lower surface, an upper surface, a thickness between the lower surface and the upper surface of the plate head section, and an aperture extending between the lower surface and the upper surface of the plate head section; and a plate neck portion being attached at one end to the plate body section, being attached at the other end to the plate head section, and extending upwardly and outwardly from the plate body section; where the plate neck portion spaces the upper surface of the plate head section from the upper surface of the plate body section, and wherein a screw head portion of a screw section is positionable upwardly and downwardly via rotation of the screw section relative to the aperture in the plate head portion between a minimum first height and a maximum second height relative to the upper surface of the plate head section, the second height being greater than the first height.

The details of one or more aspects of the disclosure as set forth in the accompanying drawings and the description below. Other features, objects, and advantages of the techniques described in this disclosure will be apparent from the description and drawings, and from the claims.

BRIEF DESCRIPTION OF DRAWINGS

FIG. 3 is a top, front, exploded perspective view that illustrates the plate system of FIG. 1;

DETAILED DESCRIPTION

Figure 1:
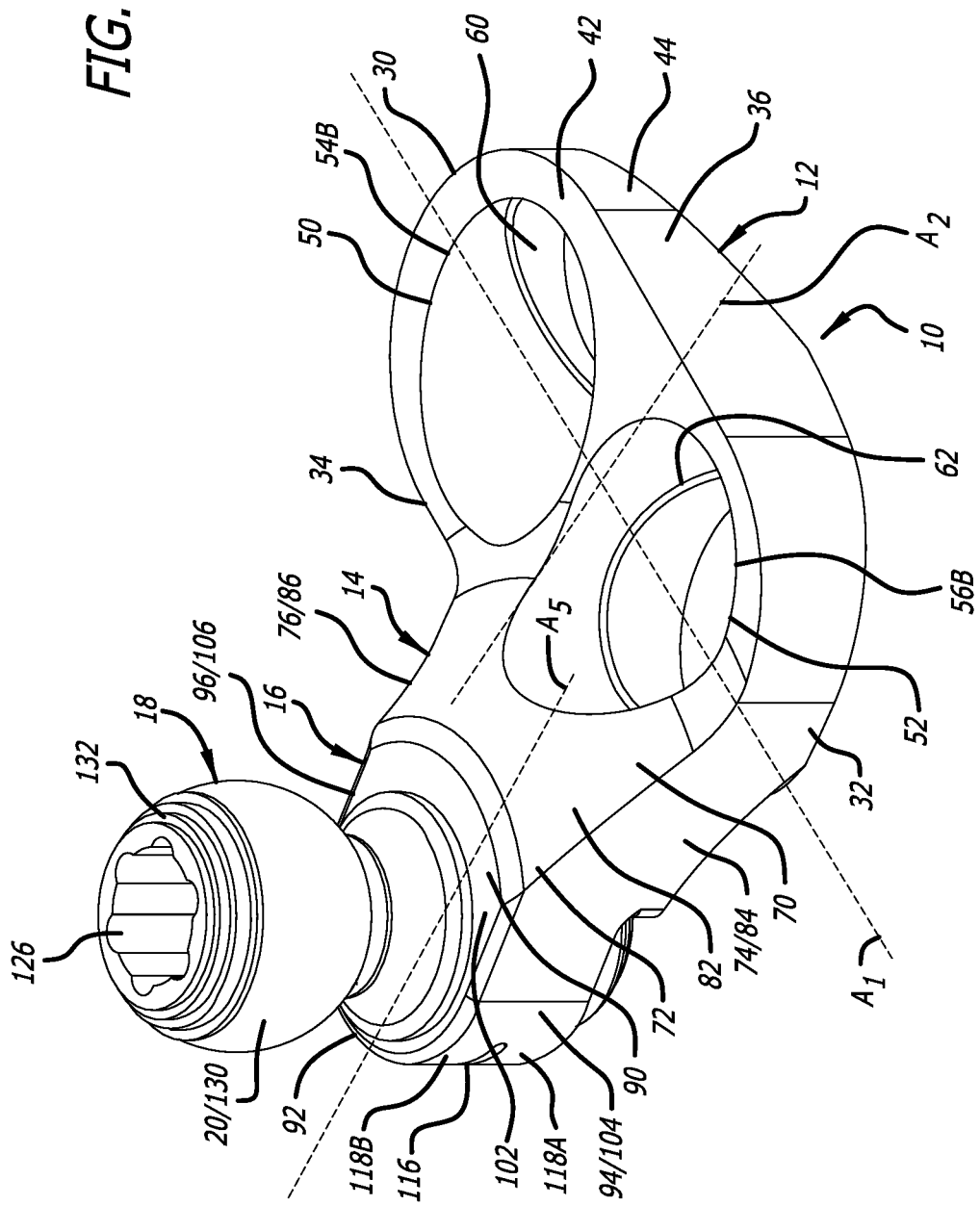
FIG. 1 is a top, front perspective view that illustrates a first embodiment of an adjustable-height bone plate system.
Figure 2:
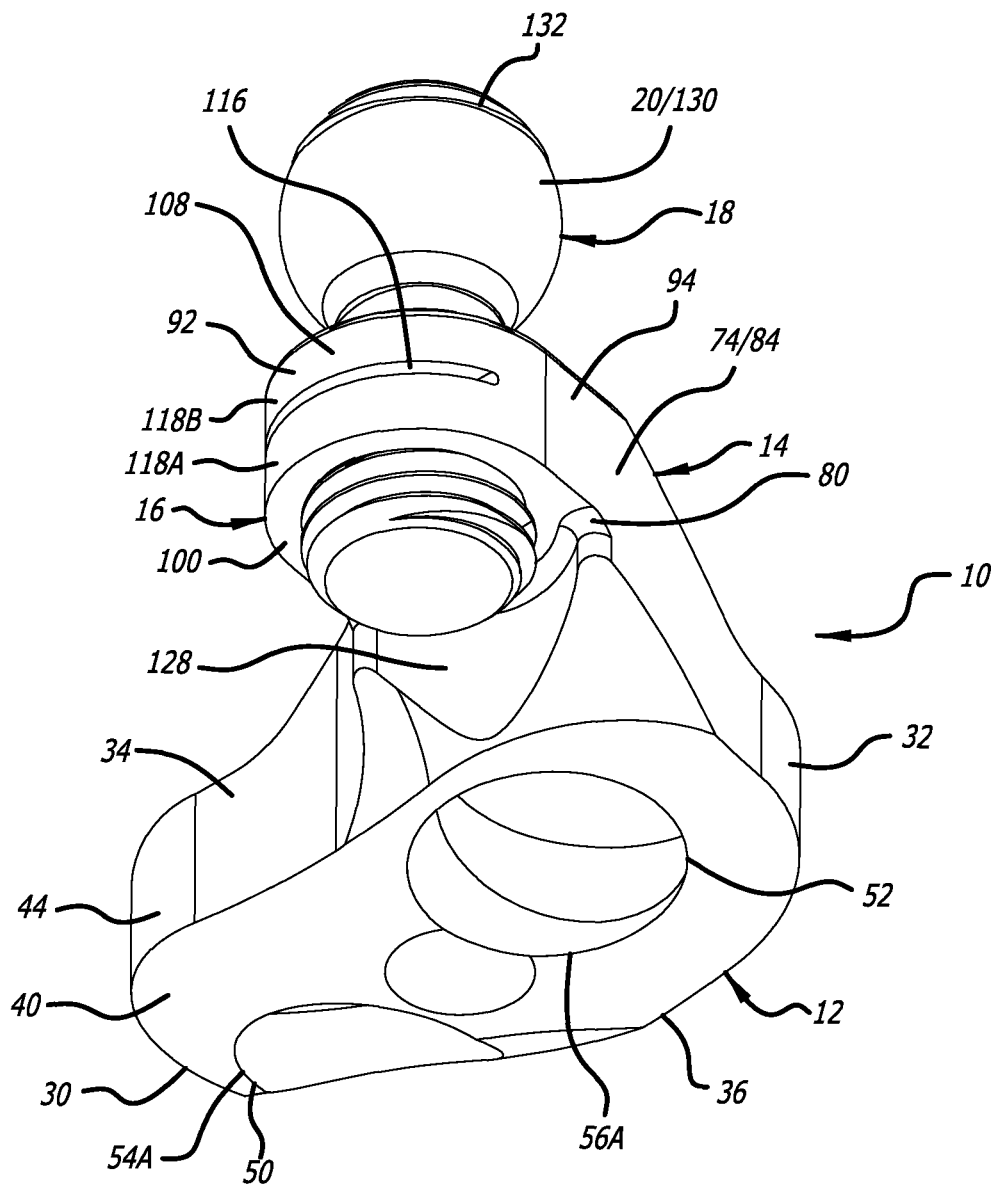
FIG. 2 is a bottom, rear perspective view that illustrates the plate system of FIG. 1.

An adjustable-height bone plate system according to an embodiment of the present disclosure is generally indicated by the numeral 10 in FIGS. 1-3. The plate system 10 can be attached to bone such as, for example, a sacrum. As such, the plate system 10 can be a sacral bone plate system. The plate system 10 includes a plate body section or portion 12, a plate neck section or portion 14, a plate head section or portion 16, and a screw section or portion 18. The plate head portion 16 is spaced apart from the plate body portion 12 by the plate neck portion 14, and the screw portion 18 is adjustable upwardly and downwardly relative to the plate head portion 16. The spacing and adjustability of the plate system 10 afford positioning of a screw head portion 20 at a proper, recommended, or desired height to facilitate interconnection with additional surgical instrumentation such as, for example, a receiver disclosed in U.S. Ser. No. 15/843,938, which is herein incorporated by reference in its entirety.

As depicted in FIGS. 1-3, the plate body portion 12 includes a first end 30, a second end 32, a first side 34, and a second side 36. The plate body portion 12 defines or is disposed in a first dimension or direction along a major mid-longitudinal axis $A_1$ (FIG. 1), extending through the first end 30, and in a second dimension or direction along a minor mid-longitudinal axis $A_2$ (FIG. 1), extending through the first side 34 and the second side 36. Portions of the first end 30 and the second end 32 are opposite from one another, and portions of the first side 34 and the second side 36 are opposite from one another. Furthermore, while the body portion 12 is depicted as being generally oblong in shape in FIGS. 1-3, the body portion 12 could have any of a variety of geometries including, but not limited to, arcuate and polygonal shapes, generally arcuate and polygonal shapes, or an amalgamation of generally arcuate and polygonal shapes. Furthermore, the major mid-longitudinal axis $A_1$ and the minor mid-longitudinal axis $A_2$ can be oriented according to the selected shape of the body portion 12, and the corresponding positions of the first end 30, the second end 32, the first side 34, and the second side 36 can correspondingly oriented to the orientation of the major mid-longitudinal axis $A_1$ and the minor mid-longitudinal axis $A_2$. Moreover, the first end 30, the second end 32, the first side 34, and/or the second side 36 could be part of the same continuous side or sides of the body portion 12. The plate body portion 12 further includes a lower surface 40, an upper surface 42, and a perimeter surface 44. The lower surface 40 and the upper surface 42 extend between the first end 30, the second end 32, the first side 34, and the second end 36. Furthermore, the perimeter surface 44 extends around the plate body portion 12, and traverses the first end 30, the second end 32, the first side 34, and the second side 36. Thicknesses of the plate body portion 12 between the lower surface 40 and the upper surface 42 can vary, and such varied thicknesses can be seen in the variable height of the perimeter surface 44. The lower surface 40 can be configured for placement against bone, and can be correspondingly contoured to conform to the bone.

The plate body portion 12 includes a first aperture 50 and a second aperture 52 positioned adjacent one another and extending between the lower surface 40 and the upper surface 42. The first aperture 50 includes a first opening 54A in the lower surface 40, a second opening 54B in the upper surface 42, and a central axis $A_3$, and the second aperture 52 includes a first opening 56A in the lower surface 40, a second opening 56B in the upper surface 42, and a central axis $A_4$. The first aperture 50 and the second aperture 52 are configured to receive bone screws (not shown) therein to facilitate attachment of the plate system 10 to bone. To that end, the first aperture 50 and the second aperture 52 can include a first shoulder 60 and a second shoulder 62, respectively, facilitating impingement of the bone screws therein to attach the plate system 10 to bone. Furthermore, as depicted in FIG. 3, the axis $A_3$ and the axis $A_4$ are not aligned with one another, and can be oriented at compound angles with respect to axis $A_1$ and/or the axis $A_2$. As such, the bone screws inserted into the apertures 50 and 52 and can be oriented at different angles in order to affix the plate body portion 12 (and hence, the plate system 10) to bone.

The plate neck portion 14 extends upwardly and outwardly from the plate body portion 12 to space the plate head portion 16 from the plate body portion 12. As depicted in FIGS. 1-3, the plate neck portion 14 includes a first end 70, a second end 72, a first side 74, a second side 76, and a mid-longitudinal axis $A_5$ extending through the first end 70 and the second end 72. Portions of the first end 70 and the second end 72 are opposite from one another, and portions of the first side 74 and the second side 76 are opposite from one another. The first end 70 of the plate neck portion 14 is attached to the plate body portion 12, and the second end 72 of the plate neck portion 14 is attached to the plate head portion 16. The plate neck portion 14 further includes a lower surface 80, an upper surface 82, a first side surface 84, and a second side surface 86. The upper surface 82 can be contiguous with and transition smoothly into the upper surface 42 of the plate body portion 12, and the first side surface 84 (at the first side 74) and the second side surface 86 (at the second side 76) each can be contiguous with and transition smoothly into the perimeter surface 44 of the plate body portion 12.

The plate head portion 16 extends outwardly from the plate neck portion 14, and, as discussed below, the plate head portion 16 is configured to receive a portion of the screw portion 18 therethrough. The plate head portion 16 is spaced apart from the plate body portion 12 by the plate neck portion, and the plate body portion 12 and the plate head portion 16 can reside in planes substantially parallel to one another. The plate head portion 16, as depicted in FIGS. 1-3, includes a first end 90, a second end 92, a first side 94, a second side 96. Portions of the first end 90 and the second end 92 are opposite from one another, and portions of the first side 94 and the second side 96 are opposite from one another. The first end 90 of the plate head portion 16 is attached to the second end 72 of the plate neck portion 14. The plate head portion 16 further includes a lower surface 100, an upper surface 102, a first side surface 104, a second side surface 106, an end surface 108. The lower surface 100 can be contiguous with and transition smoothly into portions of the lower surface 80 of the plate neck portion 14, and the upper surface 102 can be contiguous with and transition smoothly into portions of the upper surface 82 of the plate neck portion 14. Furthermore, the first side surface 104 can be contiguous with and smoothly transition into the first side surface 84 of the plate neck portion 14, and the second side surface 106 can be contiguous with and smoothly transition into the second side surface 86 of the plate neck portion 14.

Additionally, the plate head portion 16 includes an aperture 110 extending between an opening 112A in the lower surface 100 and an opening 112B in the upper surface 102. The aperture 110 includes a central axis $A_6$, and includes threads 114 extending along at least a portion thereof between the lower opening 112A and the upper opening 112B. The aperture 110 is configured to receive a portion of the screw portion 18 therein, and the screw portion 18 can be complimentarily threaded to engage the threads 114. To facilitate retention of the screw portion 18 relative to the aperture 110, the plate head portion 16 can include a slot 116 extending through the first side surface 104, the second side surface 106, and/or the end surface 108. The slot 116 extends into the plate head portion 16 and divides a portion of the plate head portion 16 into a lower portion 118A and an upper portion 118B. The slot 116 affords flexion between the lower portion 118A and the upper portion 118B, and such flexion serves in creating interference between the threads 114 and the complementary-threaded screw portion 18 to resist movement and play of the screw portion 18 in the aperture 110 to maintain the screw portion 18 in position relative to the plate head portion 16.

The screw portion 18 includes the screw head portion 20, a screw neck portion 120, a screw rim portion 121, a screw shaft portion 122, threads 124, and a central axis $A_7$. The screw neck portion 120 joins the screw rim portion 121 and the screw shaft portion 122 to the screw head portion 20. The threads 124 are formed on the screw shaft portion 122, and the threads 124 are complimentary to the threads 114 provided in the aperture 110. As discussed below, the screw portion 18 is received within the aperture 110 so that the threads 114 and 124 are engaged to one another, and rotation of the screw portion 18 serves to move the screw head portion 20 upwardly and downwardly relative to the upper surface 102 of the plate head portion 16. The screw rim portion 121 serves as a stop preventing downward movement of the screw portion 18. The above-discussed flexion between the lower portion 118A and the upper portion 118B creates interference between the threads 114 of the aperture 110 and the threads 124 formed on the screw shaft portion 122 to resist movement and play of the screw portion 18 in the aperture 110. Additionally, the perimeter surface 44 includes an indented portion 128 to avoid engagement with the screw portion 18 during rotation thereof.

A tool-engaging portion 126 is formed on the screw head portion 20 and is configured to engage a surgical tool or instrument for rotating the screw portion 18. The tool-engaging portion 126 includes six (6) lobes arranged in a generally hexagonal cross-sectional configuration. In some embodiments, the tool-engaging portion 126 has any one or more alternative cross-sectional configurations such as being generally polygonal (including generally triangular, rectangular, hexagonal, etc. configurations), oval, or irregular. Furthermore, the screw head portion 20 also includes an exterior surface 130, and, as depicted in FIGS. 1-3, the exterior surface 130 is generally spherical. The exterior surface 130 includes a plurality of ridges 132 provided adjacent the tool-engaging portion 126. The ridges 132 can be used to improve purchase of the screw head portion 20 with other surgical instrumentation such as a receiver disclosed in U.S. Ser. No. 15/843,938.

During use of the plate system 10, the plate system 10 can be attached to bone such as, for example, a sacrum. The screw portion 18 can be attached to the remainder of the plate system 10 before or after attachment of the plate system 10 to bone. After attachment of the plate system 10 to bone, the height of the screw head portion 20 relative to the upper surface 102 of the plate head portion 16 can be adjusted upwardly and downwardly via rotation of the screw portion 18 using a surgical tool or instrument. The screw head portion 20 is held in position via the flexion of the lower portion 118A and the upper portion 118B. The spacing of the plate head portion 16 apart from the plate body portion 12 by the plate neck portion 14, and the adjustment of the height of the screw head portion 20 affords positioning thereof so that, for example, a receiver disclosed in U.S. Ser. No. 15/843,938 can be attached to the screw head portion 20 at a proper, recommended, or desired height to facilitate interconnection with additional surgical instrumentation. If necessary, the height of the screw head portion 20 after attachment of such a receiver thereto can be adjusted. Additional surgical instrumentation such as, for example, a surgical rod can be attached to the receiver at a proper, recommended, or desired height for secure interconnection of the spinal rod with a receiver of a pedicle screw assembly attached to an adjacent bony structure (e.g., L5 of the lumbar spine). As such, the spacing of the plate head portion 16 apart from the plate body portion 12 by the plate neck portion 14, and the height adjustment of the screw head portion 20 relative to the plate head portion 16 affords placement of additional surgical instrumentation.

Figure 4:
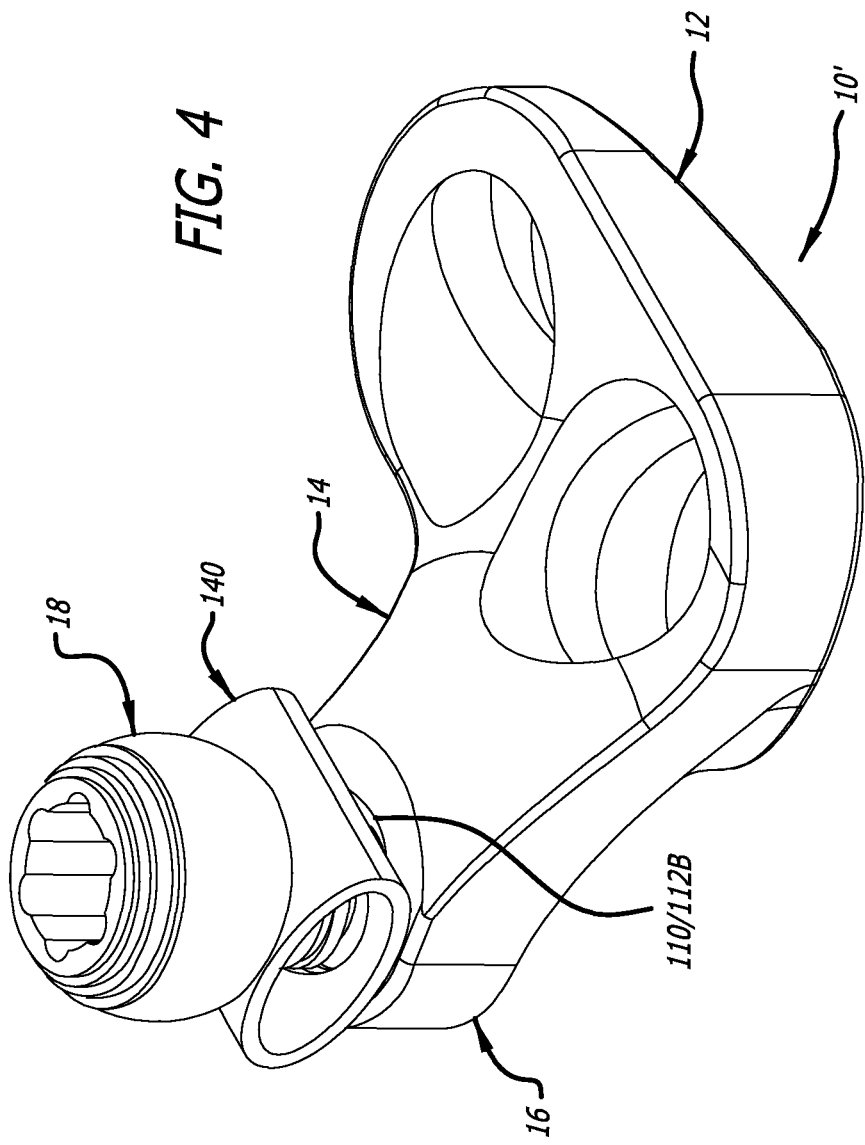
FIG. 4 is a top, front perspective view that illustrates a second embodiment of an adjustable-height bone plate system.
Figure 5:
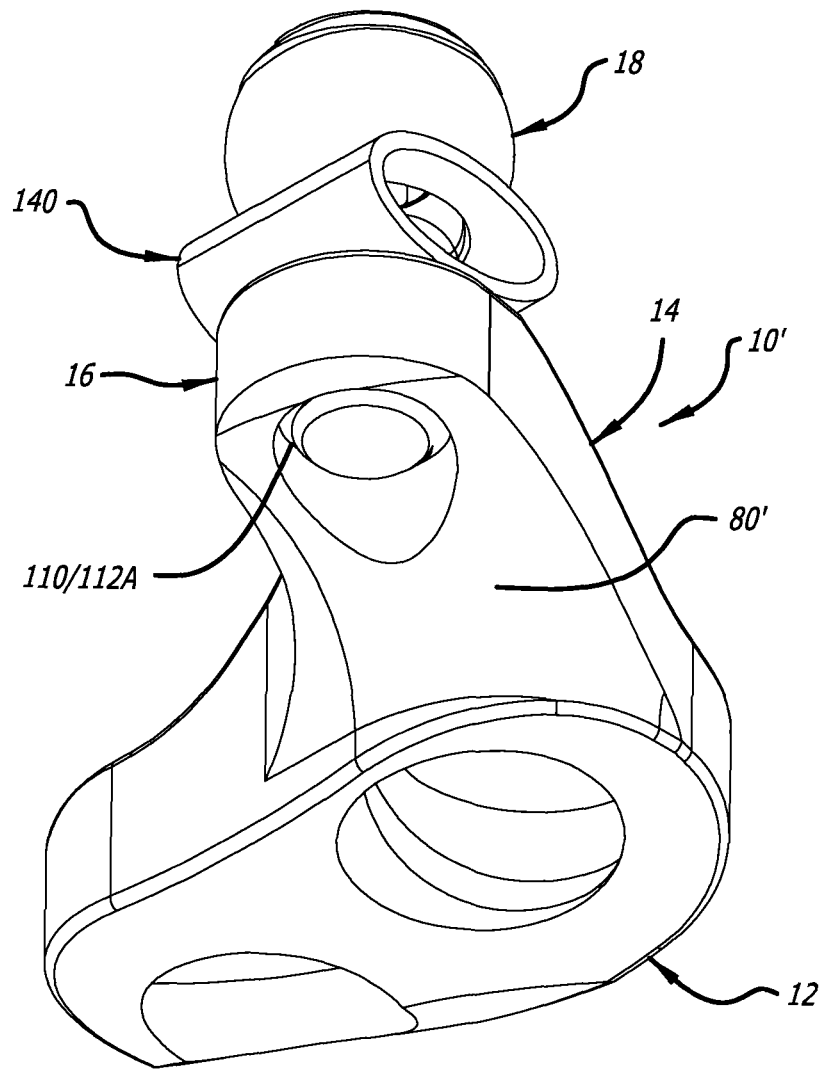
FIG. 5 is a bottom, rear perspective view that illustrates the plate system of FIG. 4.
Figure 6:
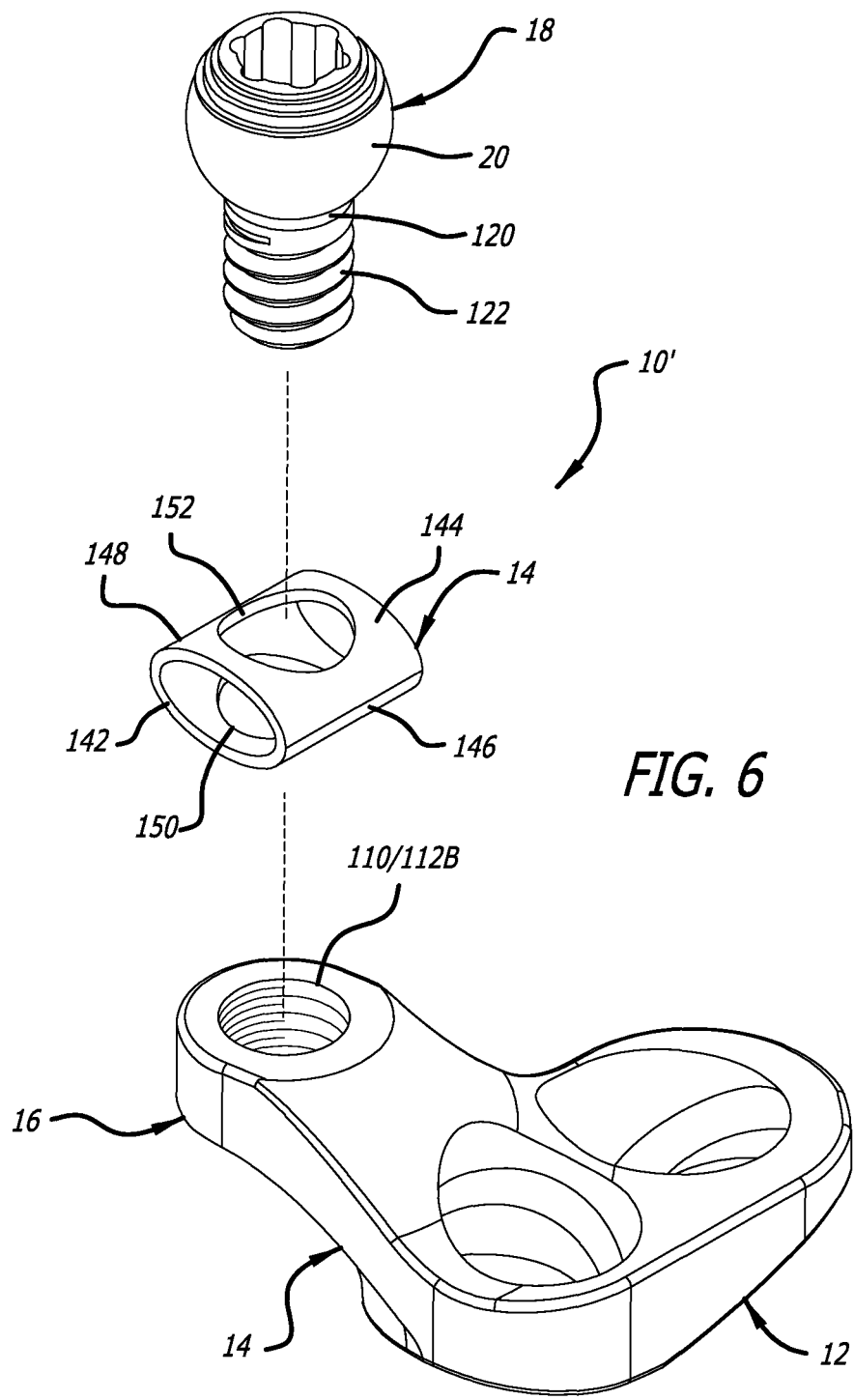
FIG. 6 is a top, front, exploded perspective view that illustrates the plate system of FIG. 4.

A plate system according to another embodiment of the present disclosure is generally indicated by the numeral 10' in FIGS. 4-6. The plate system 10' is very similar to the plate system 10 and the above description and like element numbering are generally applicable thereto, except that, for example, the plate system 10' does not include the screw rim portion 121, does not include the indentation 128, and does not include the slot 116. Rather than including the screw rim portion 121, a screw portion 18 of the plate system 10' includes a screw neck portion 120 attaching a screw head 20 directly to a screw shaft portion 122. Furthermore, rather than including the indentation 128, a neck portion 14 of the plate system 10' includes a lower surface 80', as depicted in FIG. 5. Also, rather than including the slot 116 to resist movement and play of the screw portion 18 in the aperture 110 to maintain the screw portion 18 in position relative to the plate head portion 16, the plate system 10' includes a spring (in the form of a shim, for example) 140 to create interference between the threads 114 of the aperture 110 and the threads 124 formed on the screw shaft portion 122, to resist movement and play of the screw portion 18 in the aperture 110, to correspondingly maintain or better maintain the position of the screw head portion 20.

The spring shim 140 includes a lower portion 142, an upper portion 144, a first end portion 146, and a second end portion 148. The first end portion 146 and the second end portion 148 join the lower portion 142 and the upper portion 144 to one another. Furthermore, the lower portion 142 and the upper portion 144 include a first aperture 150 and a second aperture 152, respectively. The first aperture 150 and the second aperture 152 are configured to receive the screw shaft portion 122 therethrough.

The first end portion 146 and the second end portion 148 bias the spring shim 140 in the position depicted in FIGS. 4-6. The first end portion 146 and the second end portion 148 each have a modulus of elasticity and a corresponding spring force that resists deformation of the spring shim 140 by resisting movement of the lower portion 142 and the upper portion 144 toward one another. As such, when the plate system 10' is assembled, the screw shaft portion 122 is inserted through the first aperture 150 and the second aperture 152 and into the aperture 110 so that the lower portion 142 impinges against the upper surface 102 of the plate head portion 16, and the upper portion 144 impinges against the screw head portion 20. Such impingement and the spring force of the spring shim 140 creates interference between the threads 114 of the aperture 110 and the threads 124 formed on the screw shaft portion 122 to resist movement and play of the screw portion 18 in the aperture 110 to correspondingly maintain the position of the screw head portion 20.

Figure 7:
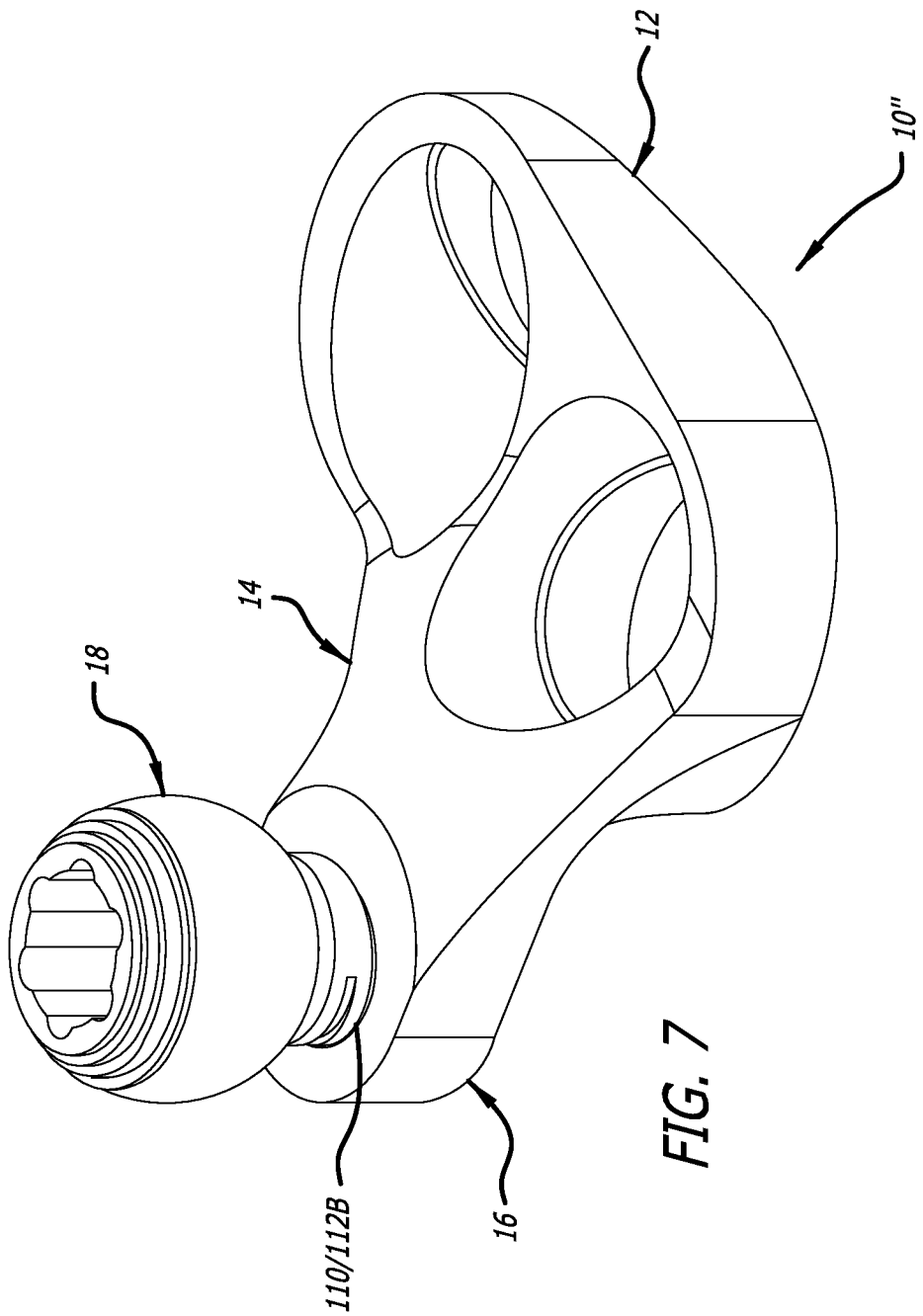
FIG. 7 is a top, front perspective view that illustrates a third embodiment of an adjustable-height bone plate system.
Figure 8:
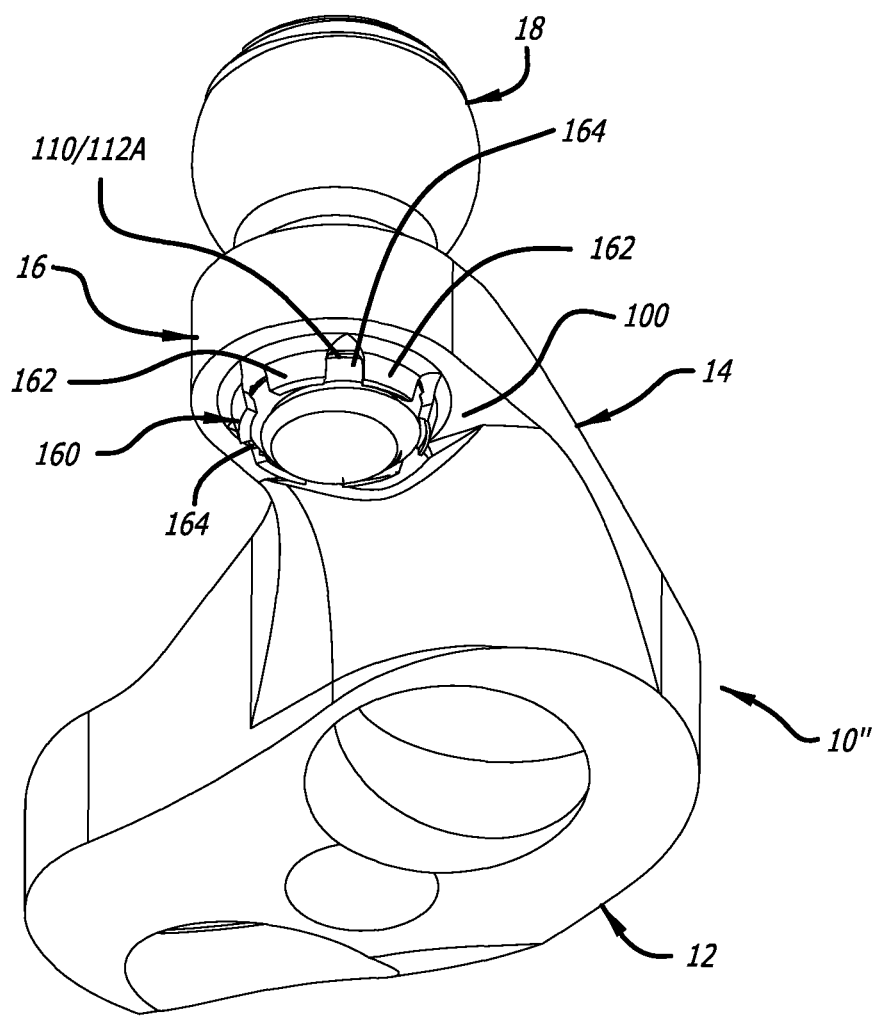
FIG. 8 is a bottom, rear perspective view that illustrates the plate system of FIG. 7.
Figure 9:
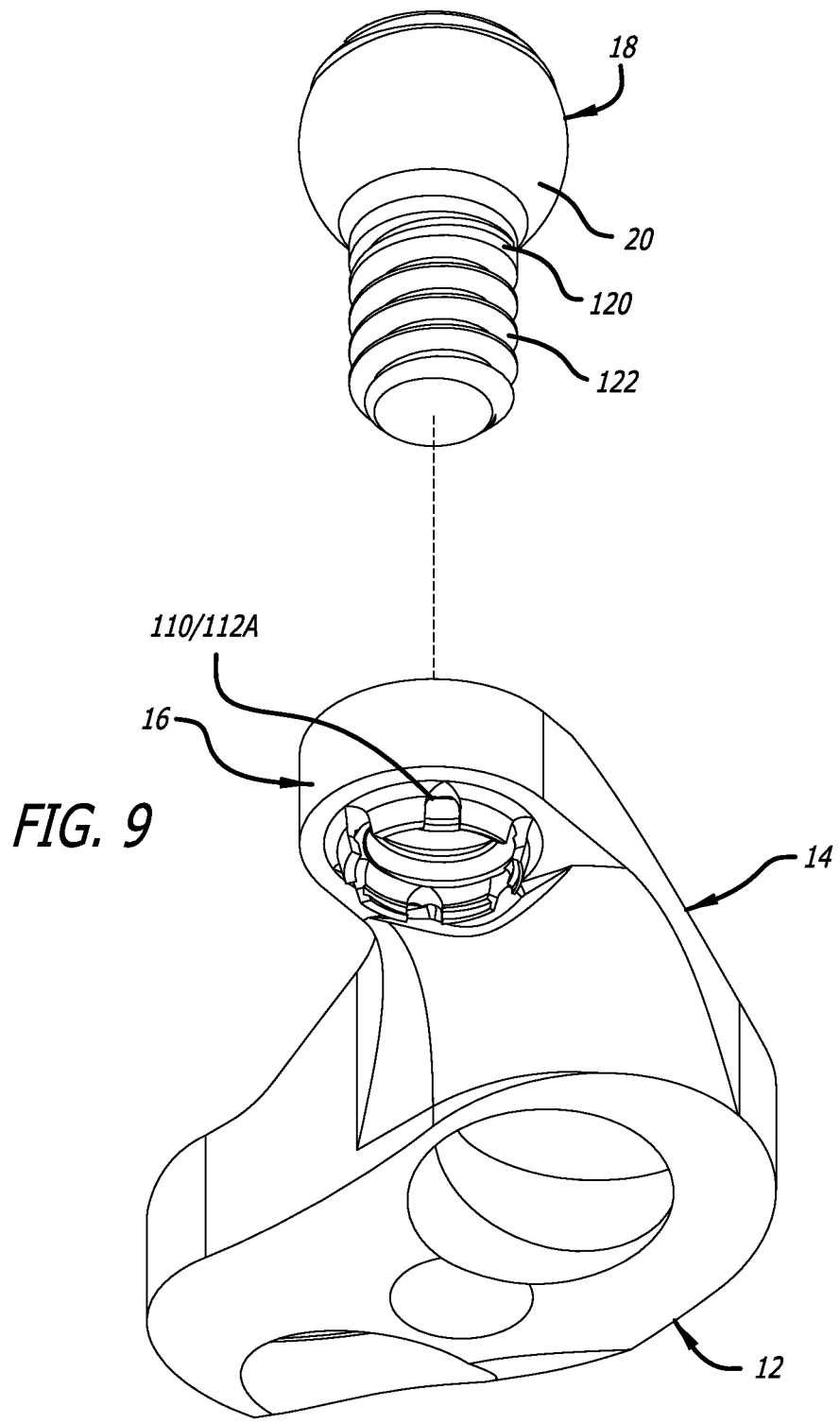
FIG. 9 is a bottom, front, exploded perspective view that illustrates the plate system of FIG. 7.

A plate system according to another embodiment of the present disclosure is generally indicated by the numeral 10" in FIGS. 7-9. The plate system 10" is very similar to the plate systems 10 and 10', and the above description and like element numbering are generally applicable thereto. For example, the plate system 10", like the plate system 10', does not include the screw rim portion 121, does not include the indentation 128, and does not include the slot 116. Furthermore, rather than including the slot 116, the plate system 10" includes crenulations 160 extending downwardly from the lower surface 100 of the plate head portion 16 and surrounding the opening 112A in the lower surface 100 of the plate head portion 16. The crenulations 160 are formed by various protrusions 162 and spaces 164 between the protrusions 162. The crenulations 160 are biased in the position depicted in FIG. 9, and the protrusions 162 each have a modulus of elasticity and a corresponding spring force that resist deformation thereof. The protrusions 162 extend into the path of and impinge against the screw shaft portion 122 when the screw portion 18 is inserted into and through the aperture 110. The impingement of the protrusions 162 against the screw shaft portion 122 causes interference therebetween to resist movement and play of the screw portion 18 in the aperture 110 to correspondingly maintain the position of the screw head portion 20.

Figure 10:
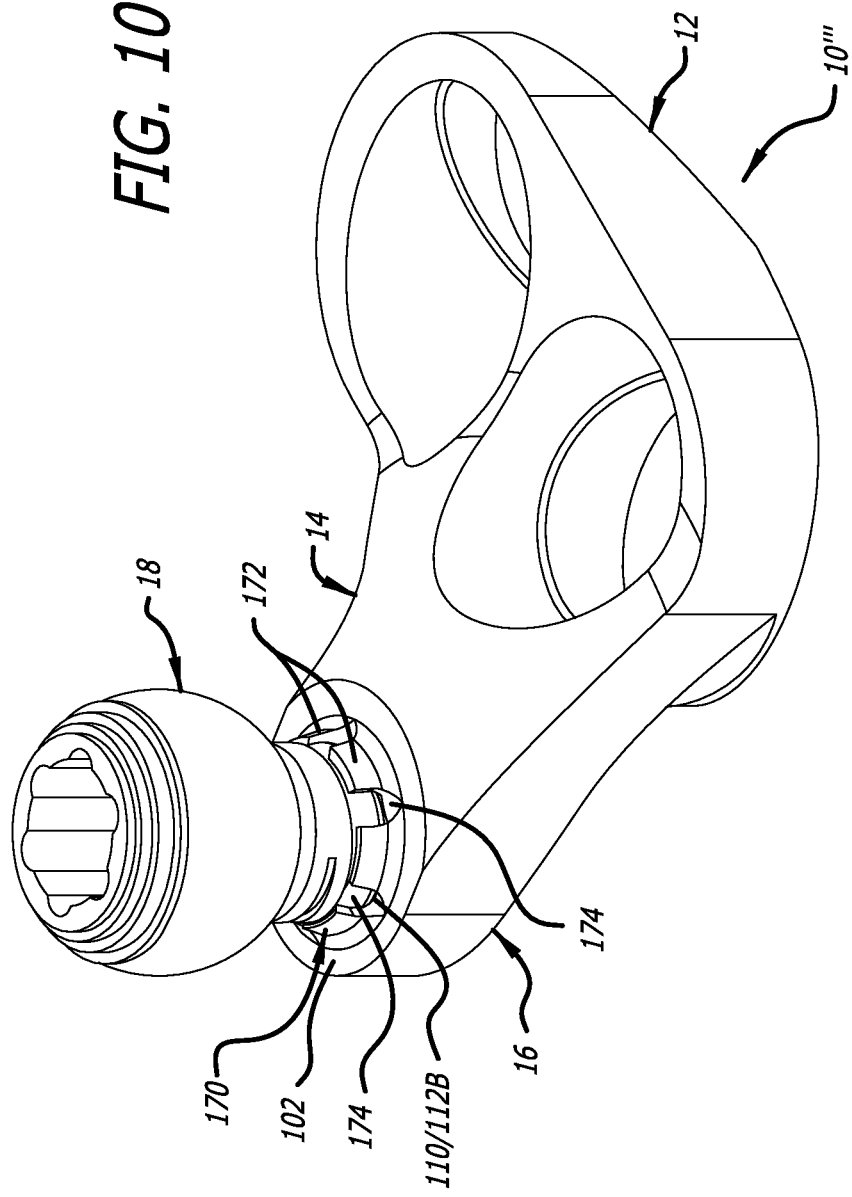
FIG. 10 is a top, front perspective view that illustrates a fourth embodiment of an adjustable-height bone plate system.
Figure 11:
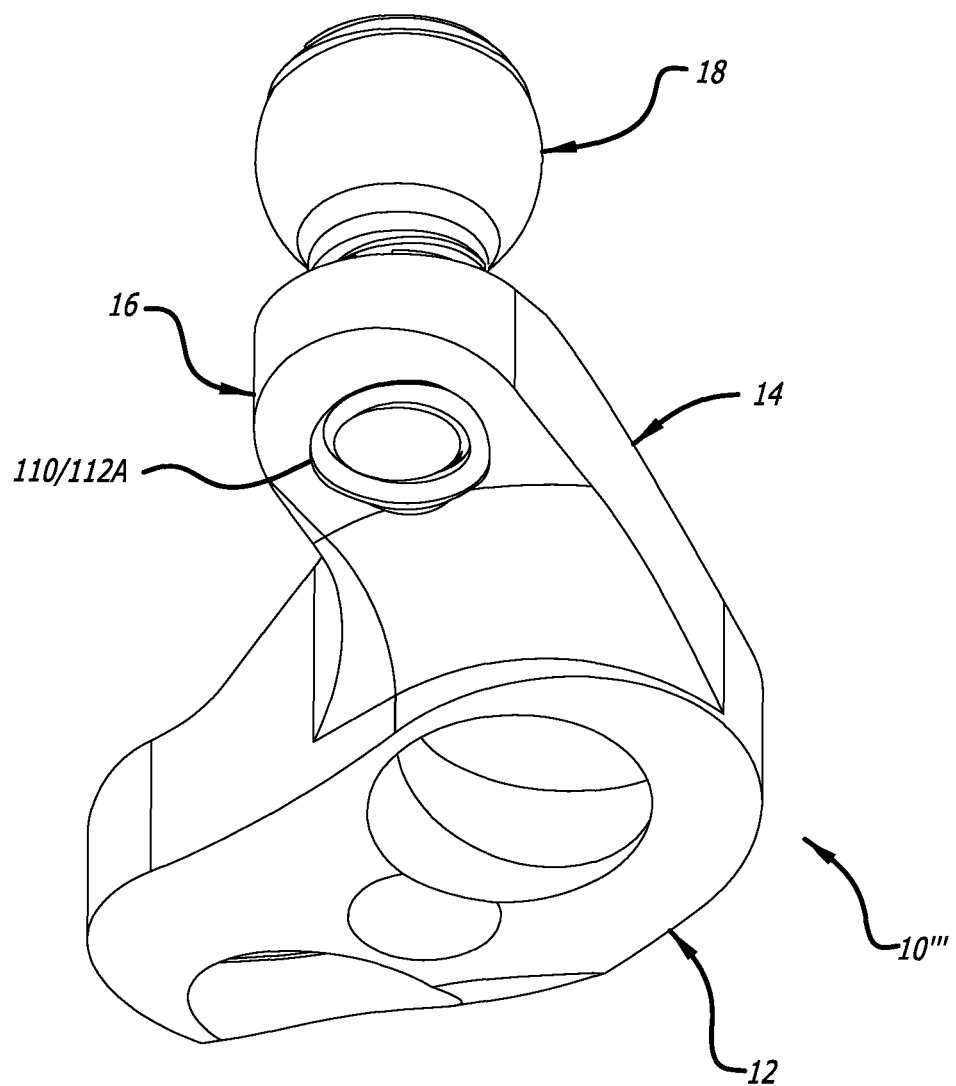
FIG. 11 is a bottom, rear perspective view that illustrates the plate system of FIG. 10.
Figure 12:
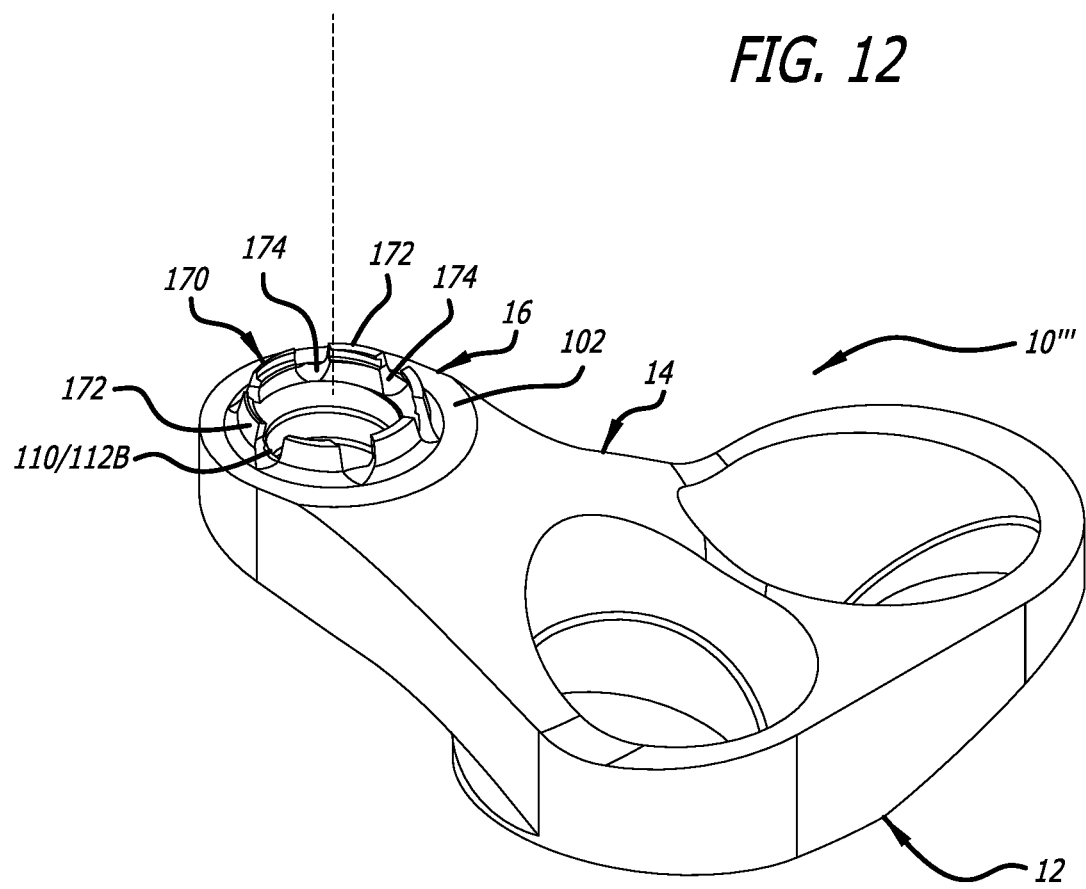
FIG. 12 is a top, front, exploded perspective view that illustrates the plate system of FIG. 10.

A plate system according to another embodiment of the present disclosure is generally indicated by the numeral 10''' in FIGS. 10-12. The plate system 10''' is very similar to the plate systems 10, 10', and 10", and the above description and like element numbering are generally applicable thereto. For example, the plate system 10''', like the plate system 10' and 10", does not include the screw rim portion 121, does not include the indentation 128, and does not include the slot 116. Furthermore, rather than including the slot 116, the plate system 10''' includes crenulations 170 extending upwardly from the upper surface 102 of the plate head portion 16 and surrounding the opening 112B in the upper surface 102 of the plate head portion 16. The crenulations 170 are formed by various protrusions 172 and spaces 174 between the protrusions 172. The crenulations 170 are biased in the position depicted in FIG. 12, and the protrusions 172 each have a modulus of elasticity and a corresponding spring force that resist deformation thereof. The protrusions 172 extend into the path of and impinge against the screw shaft portion 122 when the screw portion 18 is inserted into and through the aperture 110. The impingement of the protrusions 172 against the screw shaft portion 122 causes interference therebetween to resist movement and play of the screw portion 18 in the aperture 110 to correspondingly maintain the position of the screw head portion 20.

It should be understood that various aspects disclosed herein may be combined in different combinations than the combinations specifically presented in the description and the accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

We claim:

1. A system comprising:
a plate body section having a first end, a second end, a first side, a second side, a lower surface, an upper surface, a first thickness between the lower surface and the upper surface, and at least one aperture extending between the lower surface and the upper surface, portions of the first end and the second end being opposite from one another, portions of the first side and the second side being opposite from one another, the lower surface being configured to contact bone, and the at least one aperture being configured to receive a bone screw to facilitate attachment of the plate body section to bone;
a plate head section having a first end, a second end, a lower surface, an upper surface, a second thickness between the lower surface and the upper surface of the plate head section, and an aperture extending between the lower surface and the upper surface of the plate head section; and
a plate neck section including a first end and a second end opposite from one another, the first end being attached to the plate body section, the second end being attached to the plate head portion, the plate neck section extending upwardly and outwardly from the plate body section;
wherein the plate neck section spaces the upper surface of the plate head section from the upper surface of the plate body section at least a first height, and wherein a screw head portion of a screw section is positionable upwardly and downwardly via rotation of the screw section relative to the aperture in the plate head portion between a minimum second height and a maximum third height relative to the upper surface of the plate head section, the third height being greater than the second height, and the second height being greater than the first height.

2. The system of claim 1, wherein the plate head section further includes an end surface at the second end extending between the lower surface and the upper surface, and a slot extending through the end surface and a portion of the plate head section to divide the portion of the plate head section into a lower portion and an upper portion, and wherein the slot affords flexion between the lower portion and the upper portion to cause interference between first threads provided in the aperture of the plate head section and second threads provided on a shaft portion of the screw section.

3. The system of claim 1, further comprising a spring positioned between the upper surface of the plate head section and the screw head portion, the spring including a lower portion, an upper portion, and at least a first end portion attaching the lower portion and the upper portion to one another, the at least a first end portion generating a spring force biasing the lower portion and the upper portion into a first orientation relative to one another.

4. The system of claim 3, wherein the lower portion of the spring includes a first opening, the upper portion of the spring includes a second opening, and a shaft portion of the screw section is received through the first opening and the second opening, and the spring force applied by the spring against the plate head section and the screw head portion causing interference between first threads provided in the aperture of the plate head section and second threads provided on the shaft portion of the screw section.

5. The system of claim 4, wherein the spring further includes a second end portion attaching the lower portion and the upper portion to one another, the first end portion and the second end portion being on opposite ends of the spring and biasing the lower portion and the upper portion into the first orientation relative to one another.

6. The system of claim 1, wherein the plate head section includes crenulations extending downwardly from the lower surface of the plate head section and being provided adjacent at least a portion of the aperture in the plate head section, the crenulations including at least two tabs and a space between the at least two tabs, the at least two tabs extending into the path of and impinging on a shaft portion of the screw section received into and through the aperture of the screw head portion, the impingement of the at least two tabs on the shaft portion causing interference between first threads provided in the aperture of the plate head section and second threads provided on the shaft portion of the screw section.

7. The system of claim 1, wherein the plate head section includes crenulations extending upwardly from the upper surface of the plate head section and being provided adjacent at least a portion of the aperture in the plate head section, the crenulations including at least two tabs and a space between the at least two tabs, the at least two tabs extending into the path of and impinging on a shaft portion of the screw section received into and through the aperture of the screw head portion, the impingement of the at least two tabs on the shaft portion causing interference between first threads provided in the aperture of the plate head section and second threads provided on the shaft portion of the screw section.

8. A system comprising:
a plate body section attachable to bone, the plate body section having a first end, a second end, a first side, a second side, a lower surface, an upper surface, at least a portion of the first end and the second end of the plate body section being opposite from one another, and at least a portion of the first side and the second side being opposite from one another, and the lower surface of the plate body section being configured to contact bone;
a plate head section having a first end, a second end, a lower surface, an upper surface, a thickness between the lower surface and the upper surface of the plate head section, and an aperture extending between the lower surface and the upper surface of the plate head section; and
a plate neck portion including a first end and a second end opposite from one another, the first end being attached to the plate body section, the second end being attached to the plate head section, the plate neck portion extending upwardly and outwardly from the plate body section to space the plate body section and the plate head section apart from one another;
wherein the plate neck portion spaces the upper surface of the plate head and wherein a screw head portion of a screw section is positionable upwardly and downwardly via rotation of the screw section relative to the aperture in the plate head portion between a minimum second height and a maximum third height relative to the upper surface of the plate head section, the third height being greater than the second height and the second height being greater than the first height.

9. The system of claim 8, wherein the plate head section further includes an end surface at the second end extending between the lower surface and the upper surface, and a slot extending through the end surface and a portion of the plate head section to divide the portion of the plate head section into a lower portion and an upper portion, and wherein the slot affords flexion between the lower portion and the upper portion to cause interference between first threads provided in the aperture of the plate head section and second threads provided on a shaft portion of the screw section.

10. The system of claim 8, further comprising a spring positioned between the upper surface of the plate head section and the screw head portion, the spring including a lower portion, an upper portion, and at least a first end portion attaching the lower portion and the upper portion to one another, the at least a first end portion generating a spring force biasing the lower portion and the upper portion into a first orientation relative to one another.

11. The system of claim 10, wherein the lower portion of the spring includes a first opening, the upper portion of the spring includes a second opening, and a shaft portion of the screw section is received through the first opening and the second opening, and the spring force applied by the spring against the plate head section and the screw head portion causing interference between first threads provided in the aperture of the plate head section and second threads provided on the shaft portion of the screw section.

12. The system of claim 11, wherein the spring further includes a second end portion attaching the lower portion and the upper portion to one another, the first end portion and the second end portion being on opposite ends of the spring and biasing the lower portion and the upper portion into the first orientation relative to one another.

13. The system of claim 8, wherein the plate head section includes crenulations extending downwardly from the lower surface of the plate head section and being provided adjacent at least a portion of the aperture in the plate head section, the crenulations including at least two tabs and a space between the at least two tabs, the at least two tabs extending into the path of and impinging on the shaft portion received into and through the aperture of the screw head portion, the impingement of the at least two tabs on the shaft portion causing interference between first threads provided in the aperture of the plate head section and second threads provided on a shaft portion of the screw section.

14. The system of claim 8, wherein the plate head section includes crenulations extending upwardly from the upper surface of the plate head section and being provided adjacent at least a portion of the aperture in the plate head section, the crenulations including at least two tabs and a space between the at least two tabs, the at least two tabs extending into the path of and impinging on the shaft portion received into and through the aperture of the screw head portion, the impingement of the at least two tabs on the shaft portion causing interference between first threads provided in the aperture of the plate head section and second threads provided on a shaft portion of the screw section.

15. A system comprising:
a plate body section attachable to bone;
a plate head section having a first end, a second end, a lower surface, an upper surface, a thickness between the lower surface and the upper surface of the plate head section, and an aperture extending between the lower surface and the upper surface of the plate head section; and
a plate neck portion being attached at one end to the plate body section, being attached at the other end to the plate head section, and extending upwardly and outwardly from the plate body section;
wherein the plate neck portion spaces the upper surface of the plate head section from the upper surface of the plate body section at least a first height, and wherein a screw head portion of a screw section is positionable upwardly and downwardly via rotation of the screw section relative to the aperture in the plate head portion between a minimum second height and a maximum third height relative to the upper surface of the plate head section, the third height being greater than the second and the second height being greater than the first height.

16. The system of claim 15, wherein the plate head section further includes an end surface at the second end extending between the lower surface and the upper surface, and a slot extending through the end surface and a portion of the plate head section to divide the portion of the plate head section into a lower portion and an upper portion, and wherein the slot affords flexion between the lower portion and the upper portion to cause interference between first threads provided in the aperture of the plate head section and second threads provided on a shaft portion of the screw section.

17. The system of claim 15, further comprising a spring positioned between the upper surface of the plate head section and the screw head portion, the spring including a lower portion, an upper portion, and at least a first end portion attaching the lower portion and the upper portion to one another, the at least a first end portion generating a spring force biasing the lower portion and the upper portion into a first orientation relative to one another.

18. The system of claim 17, wherein the lower portion of the spring includes a first opening, the upper portion of the spring includes a second opening, and a shaft portion of the screw section is received through the first opening and the second opening, and the spring force applied by the spring against the plate head section and the screw head portion causing interference between first threads provided in the aperture of the plate head section and second threads provided on the shaft portion of the screw section.

19. The system of claim 15, wherein the plate head section includes crenulations extending downwardly from the lower surface of the plate head section and being provided adjacent at least a portion of the aperture in the plate head section, the crenulations including at least two tabs and a space between the at least two tabs, the at least two tabs extending into the path of and impinging on a shaft portion of the screw section received into and through the aperture of the screw head portion, the impingement of the at least two tabs on the shaft portion causing interference between first threads provided in the aperture of the plate head section and second threads provided on the shaft portion of the screw section.

20. The system of claim 15, wherein the plate head section includes crenulations extending upwardly from the upper surface of the plate head section and being provided adjacent at least a portion of the aperture in the plate head section, the crenulations including at least two tabs and a space between the at least two tabs, the at least two tabs extending into the path of and impinging on a shaft portion of the screw section received into and through the aperture of the screw head portion, the impingement of the at least two tabs on the shaft portion causing interference between first threads first threads provided in the aperture of the plate head section and second threads provided on the shaft portion of the screw section.

21. A system comprising:
a plate body section attachable to bone;
a plate head section having a first end, a second end, a lower surface, an upper surface, a thickness between the lower surface and the upper surface of the plate head section, and an aperture extending between the lower surface and the upper surface of the plate head section;
a plate neck portion being attached at one end to the plate body section, being attached at the other end to the plate head section, and extending upwardly and outwardly from the plate body section; and
an interference-causing portion provided one of adjacent the upper surface of the plate head portion, the lower surface of the plate head portion, and within a portion of the plate head portion between the upper surface and the lower surface thereof;
wherein the interference-causing portion contacts portions of a screw section received in the aperture in the plate head portion to create interference between first threads provided in the aperture and second threads provided on a shaft portion of the screw section; and
wherein the plate neck portion spaces the upper surface of the plate head section from the upper surface of the plate body section at least a first height, and wherein a screw head portion of the screw section is positionable upwardly and downwardly via rotation of the screw section relative to the aperture in the plate head portion between a minimum second height and a maximum third height relative to the upper surface of the plate head section, the third height being greater than the second height, and the second height being greater than the first height.

22. A system comprising:
a plate body section attachable to bone;
a plate head section having a first end, a second end, a lower surface, an upper surface, a thickness between the lower surface and the upper surface of the plate head section, and an aperture including first threads provided therein, the aperture extending between the lower surface and the upper surface of the plate head section;
a plate neck portion being attached at one end to the plate body section, being attached at the other end to the plate head section, and extending upwardly and outwardly from the plate body section; and
a screw section including a screw head portion and a screw shaft portion, the screw shaft portion being received in the aperture, and second threads provided on the screw shaft portion engaging the first threads provided in the aperture;
an interference-causing portion provided between the screw head portion and the upper surface of the plate head section, the interference-causing portion applying force against one of the screw head portion and the screw shaft portion to cause an interference fit between the first threads and the second threads; and wherein the plate neck portion spaces the upper surface of the plate head section from the upper surface of the plate body section at least a first height, and wherein a screw head portion of the screw section is positionable upwardly and downwardly via rotation of the screw section relative to the aperture in the plate head portion between a minimum second height and a maximum third height relative to the upper surface of the plate head section, the third height being greater than the second height, and the second height being greater than the first height.

* * * * *